United States Patent [19]
Jakob et al.

[11] Patent Number: 5,116,373
[45] Date of Patent: May 26, 1992

[54] PULL-THROUGH APPLIANCE

[75] Inventors: Roland P. Jakob, Hinterkappelen; Stefan Freudiger, Bremgarten; Rudolf Koch, Berlingen; Hans Fluckiger, Ótwil, all of Switzerland

[73] Assignees: Sulzer Brothers Limited, Winterthur; Protek AG, Berne, both of Switzerland

[21] Appl. No.: 567,803

[22] Filed: Aug. 15, 1990

[30] Foreign Application Priority Data

Aug. 28, 1989 [CH] Switzerland .......................... 3108/89

[51] Int. Cl.$^5$ .............................................. A61F 2/08
[52] U.S. Cl. ........................................ 623/13; 623/66
[58] Field of Search ................... 623/1, 11, 12, 13, 16, 623/66

[56] References Cited

U.S. PATENT DOCUMENTS 4,585,458  4/1986  Kurland ................. 623/13
4,870,966  10/1989  Dellon et al. .

FOREIGN PATENT DOCUMENTS 0223370  5/1987  European Pat. Off. .
2556210  6/1985  France ..................................... 623/1

Primary Examiner—Randy C. Shay
Attorney, Agent, or Firm—Kenyon & Kenyon

[57] ABSTRACT

The pull-through appliance is made of a mesh structure formed of at least one continuous thread and a pullout thread disposed at one end of the mesh structure to prevent unraveling of the mesh structure. A hollow tube is used to facilitate drawing in of the synthetic strand and autologous strand of the prosthesis. After removal of the hollow member, the resulting package can be readily threaded through a bore in a bone. After implantation, the pull-out thread is removed and the mesh structure unraveled so as to remove the mesh structure from within the bone.

9 Claims, 3 Drawing Sheets

PULL-THROUGH APPLIANCE

This invention relates to a pull-through appliance. More particularly, this invention relates to a tubular pull-through appliance for pulling a ligament or tendon prosthesis through a passage in a bone.

As is known, various techniques have been used for the implantation of ligaments in the bone. For example, European Patent Application 0223370 describes a prosthetic ligament in the form of a tube surrounded by a sheath of polyethylene which is secured to a cord which serves as a means for pulling the ligament through a bore in a bone.

It is has also been known from German Gebrauchsmuster U8706263 to form tubes of mesh structure for transplants in knees.

In some cases, it has been known to replace ligaments or the like which are no longer usable by means of autologous "prostheses" taken from a patient only during an implantation operation. For example, a piece of patellar tendon is often used as a prosthesis for a cruciate ligament. Further, in order to prevent overloading of an organic prosthesis of this kind, it has been known to implant a synthetic ligament or tendon prosthesis in parallel relation to the organic prosthesis such as a synthetic prosthesis, for example, be in the form of a braided or woven textile band or strip or the like and may be made of plastics, for example, a polyester. Prostheses of this multiple strand kind often extend to some extent through bores or passages in an adjacent bone. However, the pulling of a prosthesis consisting of two or more strands s through a bone is often a laborious and time-consuming task for the operating surgeon.

Accordingly, it is an object of the invention to facilitate a surgeons' task in drawing a multistrand prosthesis through a bone.

It is another object of the invention to simplify the drawing of a multistrand prosthesis through a bone during an implantation procedure.

It is another object of the invention to provide a simple appliance which can be readily used by a surgeon for the implantation of a mutlistrand prosthesis.

Briefly, the invention provides a pull-through appliance for pulling through a bore in a bone. The appliance is formed of a tubular textile mesh structure for receiving at least one of a synthetic ligament or tendon prosthesis and at least one of an organic autologous ligament or tendon prosthesis wherein the mesh is formed of at least one continuous thread. In addition, the appliance includes a pull-out thread disposed at one end of the mesh structure to prevent unraveling of the mesh structure.

The mesh structure is preferably constructed of a single layer knitted fabric with a relatively long free end of thread extending therefrom. In addition, the pull-out thread has a pair of relatively long free ends extending from the mesh structure.

The pull-through appliance is sized so that a synthetic prosthesis strand and an organic autologous prosthesis strand can be drawn through the mesh structure so as to form a single unit which can be readily pulled through a bore in a bone. Once the unit has been pulled through the bone, the pull-out thread is removed, after which, the mesh structure is unraveled or "undone" by pulling on the free end of the thread. Undoing of the pull-through appliance has proved to be very simple when the mesh structure is a knitted fabric.

The threading of the various strands of the prosthesis into the appliance can be facilitated when the mesh structure is drawn over a sterilizable dimensionally stable hollow member.

These and other objects and advantages of the invention will become more apparent from the following detailed description taken in conjunction with the accompanying drawings wherein.

Figure 1:
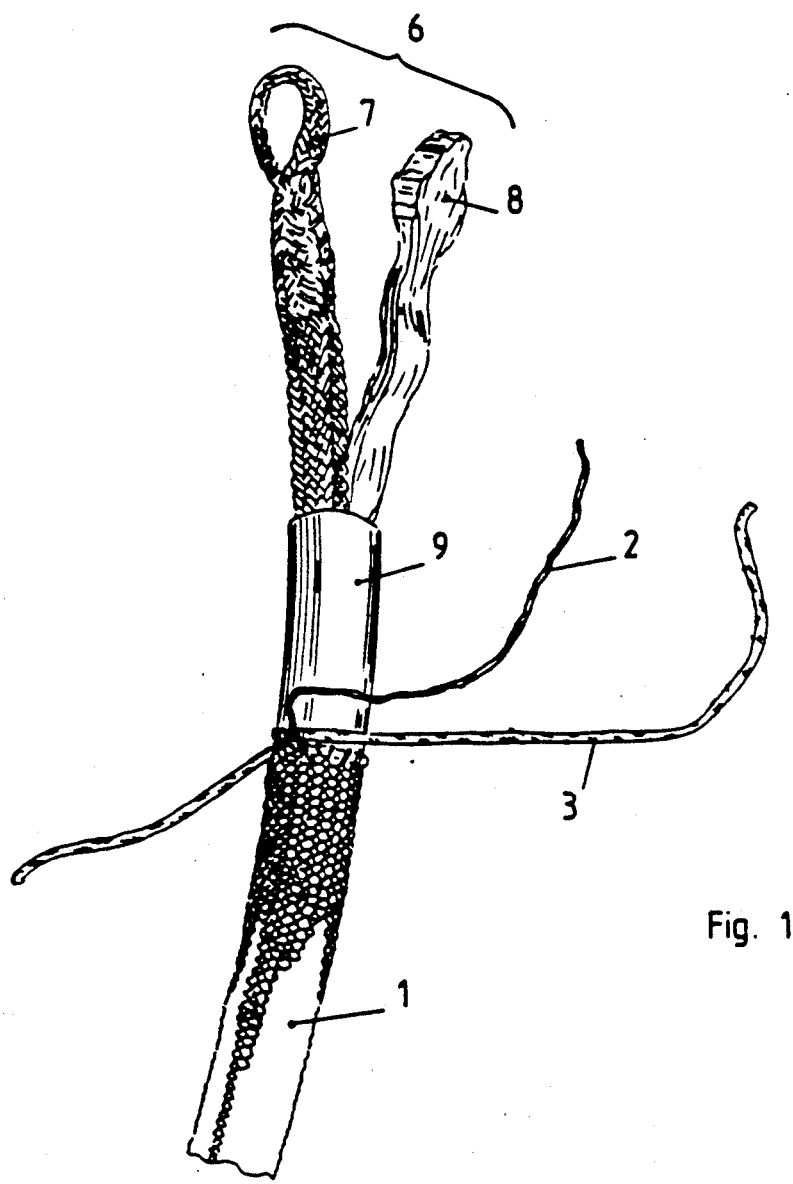
FIG. 1 illustrates a pull-through appliance drawn over a sterilizable dimensionally stable hollow member in accordance with the invention.
Figure 3:
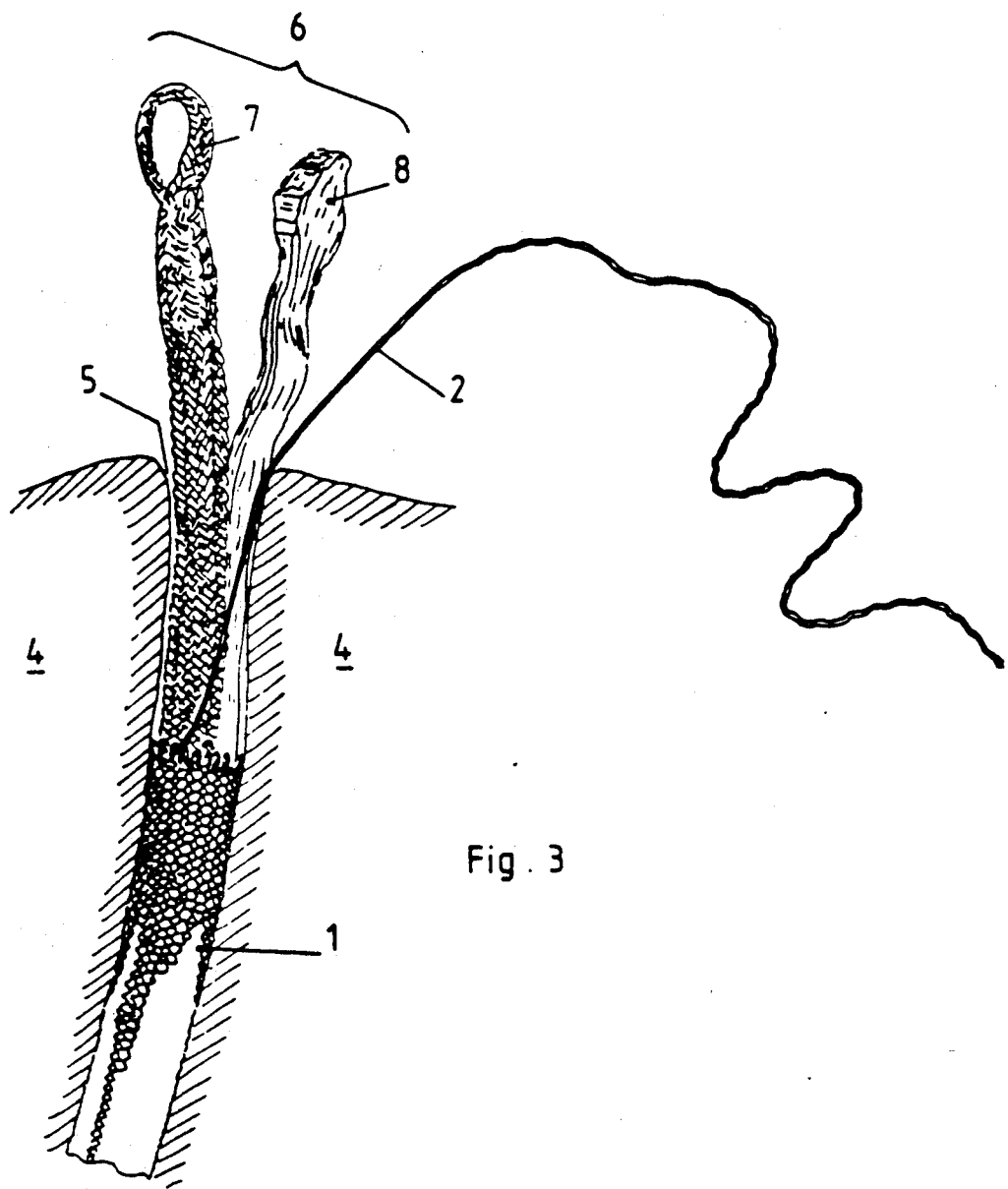
FIG. 3 diagrammatically illustrates the position of the prosthesis strands which have been drawn into a bore in a bone and which are still surrounded to some extent by the pull-through appliance.

Referring to FIG. 1, the pull-through appliance includes a tubular textile mesh structure 1 which is embodied by a single layer knitted fabric having meshes produced by a single continuous thread 2. In addition, the mesh structure 1 is provided with a pull-out thread 3 disposed at one end of the mesh structure 1 in order to prevent unraveling of the mesh structure. As indicated, the end meshes of the mesh structure 1 are retained on the pull-out thread 3. Further, the thread 2 of the mesh structure 1 has relatively long free end which extends from the mesh structure 1. Likewise, the pull-out thread 3 has a pair of relatively long free ends extending from the mesh structure 1. These thread ends are sized so as to project from a bore 5 in a bone 4 as illustrated in FIG. 3 after the pull-through appliance has been pulled through the bore 5.

The threads 2, 3 may be made primarily of plastic materials such as polyethylene, polyester or polyamides, which have been tested and proved satisfactory in the implant art. However, the pull-through appliance may also be made of surgical sewing material.

In the illustrated embodiment, the mesh structure 1 is sized so as to receive a two-strand prosthesis 6 comprised of a textile synthetic auxiliary ligament prosthesis 7 which is, for example, woven or braided and which is made of a plastic, for example, of polyester, and an organic autologous tendon prosthesis 8, for example, a piece of the patellar tendon.

In order to facilitate drawing in of the two prosthesis strands 7, 8, the mesh structure 1 is drawn over a sterilizable dimensionally stable hollow member 9. For example, the hollow member 9 is made of an appropriate plastic, such as polyester, polyethylene or polyamide.

Figure 2:
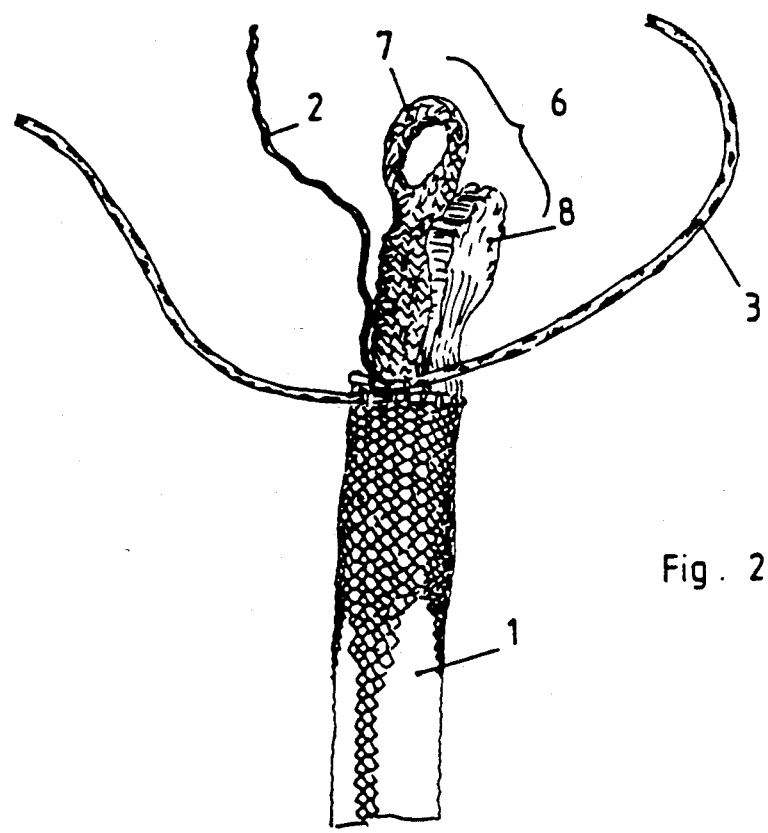
FIG. 2 illustrates a ready-to-pull-through "package" of a pull-through appliance with one organic and one synthetic strand in a prosthesis.

In use, the two strands 7, 8 are drawn through the hollow member 9. Thereafter, the hollow member 9 is removed from within the tubular mesh structure 1 so as to provide a ready-to-pull-through package as shown in FIG. 2. Next, the resulting package which forms a single strand flexible tube can be threaded by a surgeon through the bore 5 in a bone 4 in a relatively simple fashion a indicated in FIG. 3. After the flexible tube has been drawn through the bone bore 5, the surgeon first pulls the pull-out thread 3 (not shown) out of the end meshes of the mesh structure 1. Thereafter, the mesh structure 1 is unraveled (i.e. "undone") by pulling on the free end of the thread 2 so that finally only the two strands 7, 8 of the prosthesis 6 extend through the bone 4.

The invention thus provides a relatively simple pull-through appliance which can be readily used by a surgeon for the implantation of a multistrand prosthesis in a bore of a bone.

Further, the invention provides a pull-through appliance which can be readily removed after implantation by a simple unraveling of the thread by which the appliance is made.

What is claimed is:

1. A pull-through appliance for pulling through a bore in a bone comprising
    a tubular textile mesh structure for receiving at least one of a synthetic tendon prosthesis, a synthethic ligament prosthesis and at least one of an organic ligament prosthesis and an organic tendon prosthesis, said mesh being formed of at least one continuous thread having a free end extending therefrom; and
    a pull-out thread disposed at one end of said mesh structure to prevent unraveling of said mesh structure, said pull-out thread having a pair of free ends extending from said mesh structure.

2. An appliance as set forth in claim 1 wherein said mesh structure is a knitted fabric.

3. An appliance as set forth in claim 1 which further comprises a sterilizable dimensionally stable hollow member receiving said mesh structure thereon.

4. A method of drawing a multistrand prosthesis through a bone comprising the steps of
    providing a tubular textile mesh structure formed of at least one continuous thread and a pull-out thread at one end of the mesh structure;
    positioning a hollow member within the mesh structure;
    drawing at least one of an organic tendon prosthesis and an organic ligament prosthesis, and one of a synthetic ligament prosthesis and a synthetic tendon prosthesis through the hollow member;
    thereafter removing the hollow member from within the mesh structure;
    passing the mesh structure and two prostheses through a bore in a bone;
    thereafter pulling the pull-out thread from the mesh structure; and
    pulling a free end of the thread of the mesh structure to unravel the mesh structure through the bore in the bone while leaving the two prostheses in the bore.

5. In a pull-through appliance for pulling through a bore in a bone, the combination comprising
    a tubular textile mesh structure formed of at least one continuous thread;
    a pull-out thread disposed at one end of said mesh structure to prevent unraveling of said mesh structure;
    at least one organic prosthesis extending through said mesh structure; and
    at least one synthetic prosthesis extending through said mesh structure.

6. The combination as set forth in claim 5 wherein said mesh structure is a knitted fabric.

7. The combination as set forth in claim 5 which further comprises a sterilizable dimensionally stable hollow member receiving said mesh structure thereon and said prostheses therein.

8. The combination as set forth in claim 5 wherein said organic prosthesis is one of a ligament prosthesis and a tendon prosthesis.

9. The combination as set forth in claim 8 wherein said synthetic prosthesis is one of a ligament prosthesis and a tendon prosthesis.

* * * * *